United States Patent [19]

Karrer

[11] 4,065,508
[45] Dec. 27, 1977

[54] POLYPHENOXY ALKANES
[75] Inventor: Friedrich Karrer, Basel, Switzerland
[73] Assignee: Ciba-Geigy Corporation, Ardsley, N.Y.
[21] Appl. No.: 577,241
[22] Filed: May 14, 1975
[30] Foreign Application Priority Data Mar. 26, 1975 Switzerland .......................... 3969/75

[51] Int. Cl.² .............................................. C07C 43/22
[52] U.S. Cl. ......................... 260/613 R; 260/340.5 R; 260/600 R; 260/592; 260/609 F; 424/341; 424/333; 424/331; 424/308; 424/337; 424/282; 560/65; 560/64
[58] Field of Search ............................ 260/613, 613 R
[56] References Cited
U.S. PATENT DOCUMENTS

| 2,079,279 | 5/1937 | Coleman et al. | 260/613 R |
| 2,248,491 | 7/1941 | Coleman et al. | 260/613 R |
| 2,326,702 | 8/1943 | Taylor | 260/613 R |
| 3,240,703 | 3/1966 | Symon et al. | 252/45.7 |
| 3,267,151 | 8/1966 | Pilleplch | 260/613 R |
| 3,963,786 | 6/1976 | Karrer et al. | 260/613 R |

Primary Examiner—Bernard Helfin
Attorney, Agent, or Firm—Harry Falber

[57] ABSTRACT

Compounds of the formula

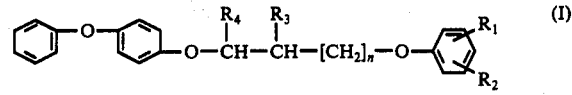

wherein
$n$ represents the number 0, 1 or 2,
$R_1$ represents hydrogen, $C_1$-$C_4$-alkyl, $C_1$-$C_2$-alkoxy, $C_3$-$C_4$-alkenyloxy, $C_3$-$C_5$-alkynyloxy, halogen, $C_1$-$C_3$-alkylcarbonyl, formyl, $C_1$-$C_5$-alkoxy-carbonyl or $C_1$-$C_2$-alkylthio,
$R_2$ represents hydrogen, $C_1$-$C_3$-alkyl, $C_1$-$C_2$-alkoxy or chlorine, or
$R_1$ and $R_2$ together represent the 3,4-methylenedioxy group,
$R_3$ represents hydrogen, methyl, ethyl or phenyl,
$R_4$ represents hydrogen or methyl, a method for their preparation, pest control agents containing them and a method of combatting pests which comprises applying to the said pests a compound of the formula are described.

10 Claims, No Drawings

POLYPHENOXY ALKANES

The present invention relates to diphenyl ethers, to processes for their production and to their use in pest control.

The diphenyl ethers have the formula

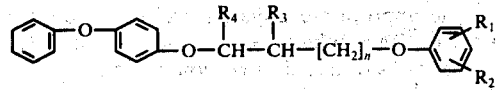 (I)

wherein
n represents the number 0, 1 or 2,
$R_1$ represents hydrogen, $C_1$-$C_4$-alkyl, $C_1$-$C_2$-alkoxy, $C_3$-$C_4$-alkenyloxy, $C_3$-$C_5$-alkynyloxy, halogen, $C_1$-$C_3$-alkylcarbonyl, formyl, $C_1$-$C_5$-alkoxycarbonyl or $C_1$-$C_2$-alkylthio,
$R_2$ represents hydrogen, $C_1$-$C_3$-alkyl, $C_1$-$C_2$-alkoxy or chlorine, or
$R_1$ and $R_2$ together represent the 3,4-methylenedioxy group,
$R_3$ represents hydrogen, methyl, ethyl or phenyl,
$R_4$ represents hydrogen or methyl.

By halogen is meant fluorine, chlorine, bromine or iodine. The alkyl, alkenyl or alkynyl groups denoted by $R_1$ and $R_2$ can be branched-chain or straight-chain. Examples of such groups are, inter alia: methyl, ethyl, propyl, isopropyl, n-, i-, sec.-, tert.-butyl, allyl, methallyl or propargyl.

Compounds of formula I particularly preferred on account of their action are those wherein n represents the number 0, 1 or 2, and $R_1$ to $R_4$ each represent hydrogen.

The compounds of formula I can be produced by the following methods known per se:

Suitable acid-binding agents or bases are, e.g., tertiary amines such as trialkylamines, pyridine, dialkylanilines; also inorganic bases such as hydrides, hydroxides, alkoxides and carbonates of alkali metals and alkaline-earth metals.

The processes 1 to 4 are performed at a reaction temperature of between 10° and 140° C, mostly between 20° and 110° C, at normal pressure and in solvents or diluents.

Suitable solvents or diluents are, e.g., ethers and ethereal compounds such as diethyl ether, di-iso-propyl ether, 1,2-dimethoxyethane, dioxane, tetrahydrofuran; carboxylic acid amides such as dimethylformamide or formamide; aliphatic and aromatic hydrocarbons, especially benzene, toluene or xylenes; dimethylsulphoxide; ketones such as acetone, methyl ethyl ketone, cyclohexanone, as well as hexamethylphosphoric acid triamide.

The starting materials of formulae II to VIII can be produced by methods analogous to known methods described in the literature.

The compounds of formula I are suitable for the control of insects of the families: Acrididae, Blattidae, Gryllidae, Gryllotalpidae, Tettigoniidae, Cimicidae, Pyrrhocoridae, Reduviidae, Aphididae, Delphacidae, Disapididae, Pseudococcidae, Chrysomelidae, Coccinellidae, Bruchidae, Scarabaeidae, Deremstidae, Tenebrionidae, Curculionidae, Tineidae, Noctuidae, Lymantriidae, Pyralidae, Galleridae, Culicidae, Tipulidae, Stomoxydae, Muscidae, Galliphoridae, Trypetidae or Pulicidae.

The insecticidal action can be substantially broadened and adjusted to suit given circumstances by the addition of other insecticides and/or acaricides. Suitable additives are, e.g.: organic phosphorus compounds, nitrophenols and derivatives thereof, formamidines, ureas, carbamates or chlorinated hydrocarbons or pyrethroids.

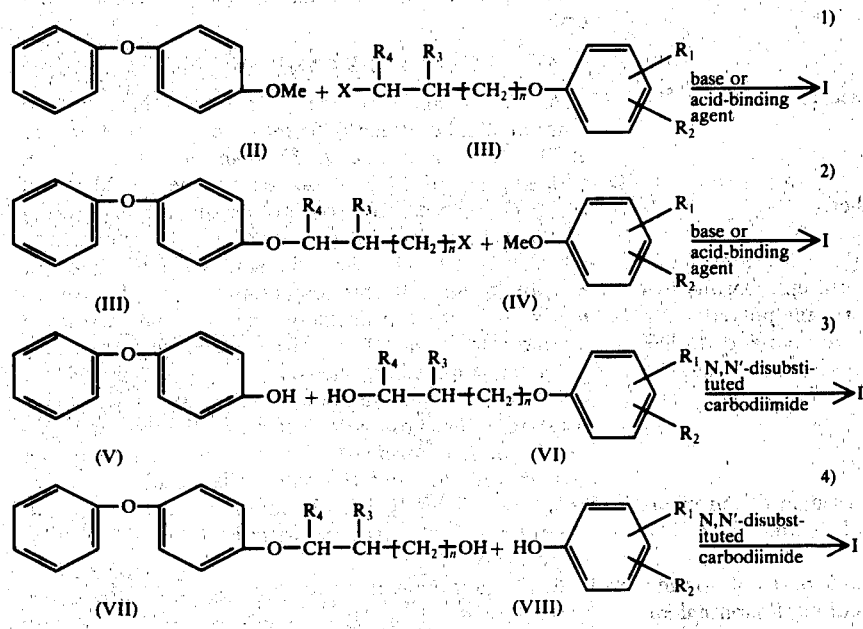

In the formulae I to VIII, the symbols n, $R_1$ to $R_4$ have the meanings given the formula I, and X stands for halogen, particularly for chlorine or bromine, —$OSO_2$—alkyl or —$OSO_2$—aryl and Me stands for a metal of the 1st or 2nd group of the periodic system, especially for sodium, potassium or calcium.

The compounds of formula I can be used on their own or together with suitable carriers and/or additives. Suitable carriers and additives may be solid or liquid, and they correspond to the substances common in formulation practice, such as natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice.

The compositions according to the invention are produced in a manner known per se by the intimate mixing and/or grinding of active substances of formula I with suitable carriers, optionally with the addition of dispersing agents or solvents that are inert to the active substances. The active substances can be obtained and used in the following forms:

Solid preparations:

Dusts, scattering agents, granulates, coated granulates, impregnated granulates and homogeneous granulates.

Liquid preparations:

a. water-dispersible active-substance concentrates: wettable powders, pastes or emulsions,
b. solutions.

The content of active substance in the described preparations is between 0.1 and 95%.

The active substances of formula I can be formulated, for example, as follows:

Dusts:

The following substances are used to prepare (a) a 5% dust, and (b) a 2% dust:
 a. 5 parts of active substance, 95 parts of talcum;
 b. 2 parts of active substance, 1 part of highly dispersed silicic acid, 97 parts of talcum.

The active substances are mixed and ground with the carriers.

Granulate:

The following substances are used to produce a 5% granulate:
 5 parts of active substance,
 0.25 part of epichlorohydrin,
 0.25 part of cetyl polyglycol ether,
 3.50 parts of polyethylene glycol,
 91 parts of kaolin (particle size 0.3 — 0.8 mm).

The active substance is mixed with epichlorohydrin and dissolved with 6 parts of acetone; the polyethylene glycol and cetyl polyglycol ether are then added. The solution thus obtained is sprayed on to kaolin, and the acetone is subsequently evaporated off in vacuo.

Wettable powder:

The following constituents are used in the preparation of (a) a 40%, (b) and (c) a 25%, and (d) a 10% wettable powder:
 a. 40 parts of active substance, 5 parts of sodium lignin sulphonate, 1 part of sodium dibutyl-naphthalene sulphonate, 54 parts of silicic acid;
 b. 25 parts of active substance, 4.5 parts of calcium lignin sulphonate, 1.9 parts of Champagne chalk/hydroxyethyl cellulose mixture (1:1), 1.5 parts of sodium dibutyl naphthalene sulphonate, 19.5 parts of silicic acid 19.5 parts of Champagne chalk, 28.1 parts of kaolin;
 c. 25 parts of active substance, 2.5 parts of isooctylphenoxy-polyoxyethylene-ethanol, 1.7 parts of Champagne chalk/hydroxyethyl cellulose mixture (1:1), 8.3 parts of sodium aluminium silicate, 16.5 parts of kieselguhr, 46 parts of kaolin;
 d. 10 parts of active substance, 3 parts of a mixture of the sodium salts of saturated fatty alcohol sulphates, 5 parts of naphthalenesulphonic acid/formaldehyde condensate, 82 parts of kaolin.

The active substances are intimately mixed, in suitable mixers, with the additives; the mixture is then ground in the appropriate mills and rollers. Wettable powders are obtained which can be diluted with water to give suspensions of any desired concentration.

Emulsifiable concentrates:

The following substances are used to produce (a) a 10%, (b) a 25% and (c) a 50% emulsifiable concentrate:
 a. 10 parts of active substance, 3.4 parts of epoxidised vegetable oil, 3.4 parts of a combination emulsifier consisting of fatty alcohol polyglycol ether and alkylarylsulphonate calcium salt, 40 parts of dimethylformamide, 43.2 parts of xylene;
 b. 25 parts of active substance, 2.5 parts of epoxidised vegetable oil, 10 parts of alkylarylsulphonate/fatty alcoholpolyglycol ether mixture, 5 parts of dimethylformamide, 57.5 parts of xylene;
 c. 50 parts of active substance, 4.2 parts of tributylphenol-polyglycol ether, 5.8 parts of calcium-dodecylbenzenesulphonate, 20 parts of cyclohexanone, 20 parts of xylene.

It is possible to prepare from these concentrates, by dilution with water, emulsions of any desired concentration.

Spray:

The following constituents are used to produce a) a 5% spray and b) a 95% spray:
 a. 5 parts of active substance, 1 part of epichlorohydrin, 94 parts of ligroin (boiling limits 160° – 190° C);
 b. 95 parts of active substance, 5 parts of epichlorohydrin.

EXAMPLE 1

A. The solution of 20.1 g of 2-bromoethyl-phenyl ether in 30 ml of dimethylformamide is added dropwise at 70° – 75° C in the course of half an hour, with stirring, to a mixture of 19 g of 4-phenoxy-phenol, 20.7 g of finely pulverised anhydrous potassium carbonate, 0.5 g of potassium iodide, 40 ml of dimethylformamide and 50 ml of hexamethylphosphoric acid triamide, and the mixture is held at this temperature for a further 24 hours. In further processing, the reaction mixture is poured into about 600 ml of ice water and repeatedly extracted with ether. The combined ether phases are repeatedly washed with cold 10% potassium hydroxide solution, afterwards with water and finally with saturated sodium chloride solution; they are then dried over sodium sulphate and the solvent is distilled off. The resulting 1-phenoxy-4-(2-phenoxy)-ethoxy-benzene that has solidified in crystalline form is recrystallised from isopropanol; m.p.: 91°–92° C.

B. 13.2 g of potassium-tert.-butoxide is added portionwise, with slight external cooling (ice water) and with the introduction of nitrogen, to a solution of 20.4 g of 4-phenoxyphenol in 200 ml of dimethylsulphoxide. After potassium-phenoxy-phenolate has formed, with complete dissolving of the potassium-tert.-butoxide, there is added dropwise to the phenolate within 30 minutes at 20°–22° C, with stirring, 21.5 g of 1-bromo-3-phenoxypropane, and the whole is stirred at 30° C for a further 16 hours. In further processing, the reaction mixture is poured, with stirring, into 800 ml of ice water, and the mixture is repeatedly extracted with dichloromethane. The combined dichloromethane phases are thereupon repeatedly washed with ice-cold 10% potassium hydroxide solution, water and saturated sodium chloride solution; they are then dried over sodium sulphate and the solvent is completely removed in vacuo. The 1-phenoxy-4-(3-phenoxy)-1-propoxy-benzene then solidifying in crystalline form is further purified by recrystallisation in isopropanol; m.p. 69°–71° C.

The following compounds can be produced in an analogous manner:

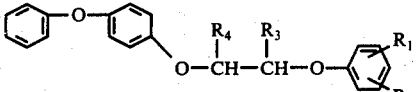

| $R_1$ | $R_2$ | $R_3$ | $R_4$ | m.p. |
|---|---|---|---|---|
| 4-$CH_3$ | H | H | H | 111–112° C |
| 3-$CH_3$ | H | H | H | 89–90° C |
| 4-$C_2H_5$ | H | H | H | 113–114° C |
| 4-$C_3H_{7(i)}$ | H | H | H | |
| 3,4-O—$CH_2$—O— | | H | H | 105–106° C |
| 4-Cl | H | H | H | 106–107° C |
| 4-$CH_3$ | 3-$CH_3$ | H | H | 93–94° C |
| 4-$CH_3$ | 2-$CH_3$ | H | H | 87–88° C |
| 4-CHO | H | H | H | 112–113° C |
| 4-Br | H | H | H | 121–122° C |
| 4-$CF_3$ | H | H | H | 90–92° C |
| 4-$COCH_3$ | H | H | H | 106–107° C |
| 2-$OC_2H_5$ | H | H | H | $n_D^{20}$: 1,5870 |
| 2-$OCH_3$ | H | H | H | 91–92° C |
| 4-$OCH_3$ | H | H | H | 111–112° C |
| 4-$SCH_3$ | H | H | H | 113–114° C |
| 4-$C_2H_5$ | H | —$CH_3$ | H | |
| 4-$CH_3$ | H | —$CH_3$ | H | |
| 4-O—$CH_2$—C≡CH | H | H | H | 90–91° C |
| 4-$CH_3$ | H | —$CH_3$ | —$CH_3$ | |
| 4-$C_2H_5$ | H | —$CH_3$ | —$CH_3$ | |
| 3,4-O—$CH_2$—O— | H | —$CH_3$ | 67–68° C | |
| 4-$CH_3$ | H | phenyl | H | |
| 4-$C_2H_5$ | H | phenyl | H | $n_D^{20}$: 1,5910 |
| 4-$C_2H_5$ | H | H | —$CH_3$ | |
| 4-$CH_3$ | H | H | —$CH_3$ | |
| 4-Cl | 2-$CH_3$ | H | H | 78–79° C |
| 2-$COOC_2H_5$ | H | H | H | 40–42° C |

| $R_1$ | $R_2$ | m.p. |
|---|---|---|
| 4-$CH_3$ | H | 65–66° C |
| 4-$C_2H_5$ | H | 55–56° C |
| 4-Cl | H | 62–63° C |
| 3-$C_2H_5$ | H | $n_D^{20}$: 1,5750 |
| 3,4-O—$CH_2$—O— | | 69–70° C |
| H | H | 69–71° C |
| 4-$C_2H_5$ | H | 83–84° C |

EXAMPLE 2

A. Contact action on Dysdercus-fasciatus larvae

A specific amount of a 0.1% acetonic active-substance solution (corresponding to 10 mg of active substance per square meter) was transferred by pipet to an aluminium dish and uniformly distributed. After evaporation of the acetone, 10 larvae in the 5th stage of Dysdercus fasciatus were placed into the treated dish containing feed and moist cotton wool. The dish was then covered with a perforated lid. After about 10 days, i.e. as soon as the control insects had moulted into adults, the test insects were examined to determine the number of normal adults.

Compounds according to Example 1 exhibited a good action in the above test.

B. Contact action on Aedes-aegypti larvae

About 20 two-day-old larvae of the yellow-fever mosquito (Aedes aegypti) were placed in position in a beaker containing a solution of the active substance (concentration 5 ppm). The beaker was then covered with a perforated lid. After the control insects had moulted into adults, the test insects were examined and the percentage of normal adults in comparison with the control adults was determined.

Compounds according to Example 1 exhibited a good action in the above test.

C. Contact action on Tenebrio-molitor pupae

A specific amount of a 0.1% acetonic active-substance solution corresponding to 10 mg of active substance per square meter was transferred by pipet into an aluminium dish and uniformly distributed. After evaporation of the acetone, 10 freshly formed pupae was placed onto the treated surface, and the dish was covered with a perforated lid. After the control insects had left the cocoon as imagines, the test insects were examined to determine the number of normal adults.

Compounds according to Example 1 exhibited a good action in the above test.

EXAMPLE 3

A. Action against Musca domestica

An amount in each case of 50 g of CSMA maggot substrate was weighed off in beakers. For each active substance, 2.5 ml of a 1% acetonic solution of the respective substance was transferred by pipet twice to 50 g of maggot substrate each time. After a thorough mixing of the treated substrate, the solvent was allowed to evaporate off. There were then deposited per active substance in each case 25 one-, two- and three-day-old maggots and about 50 fly eggs. After completion of pupation, the pupae were flushed out and counted. After a period of ten days, the number of emerged flies was counted and hence any effect on metamorphosis was established.

Compounds according to Example 1 exhibited in this test a good action against Musca domestica.

B. Action against Ephestia kuhniella 50 g of wheat flour was mixed in two beakers with a specific amount of active substance formulated as a 5% dust, so that the concentration was 0.05%. Into each beaker (25 g of flour) there were placed 10 larvae of Ephestia kuhniella. The pattern of population was ascertained over a period of 8 weeks and the number of moths determined.

Compounds according to Example 1 exhibited a good action in this test against Ephestia kuhniella.

I claim:

1. A compound of the formula

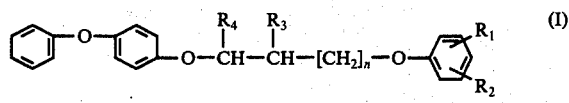

wherein
  $n$ represents the number 0, 1 or 2,
  $R_1$ represents hydrogen, $C_1$-$C_4$-alkyl, $C_1$-$C_2$-alkoxy, $C_3$-$C_4$-alkenyloxy, $C_3$-$C_5$-alkynyloxy, or halogen,
  $R_2$ represents hydrogen, $C_1$-$C_3$-alkyl, $C_1$-$C_2$-alkoxy or chlorine,
  $R_3$ represents hydrogen, methyl ethyl or phenyl, $R_4$ represents hydrogen or methyl.

2. A compound according to claim 1 wherein n represents the number 0, 1 or 2, and $R_1$ to $R_4$ each represent hydrogen.

3. The compound according to claim 2 of the formula

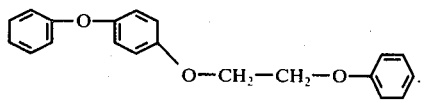

4. The compound according to claim 2 of the formula

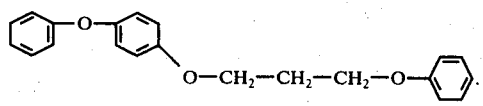

5. The compound according to claim 1 of the formula

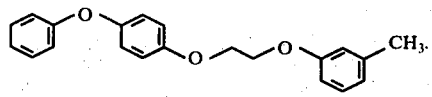

6. The compound according to claim 1 of the formula

7. The compound according to claim 1 of the formula

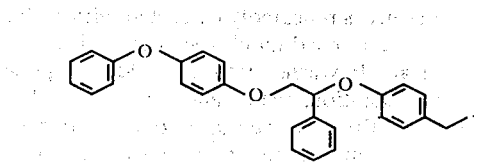

8. The compound according to claim 1 of the formula

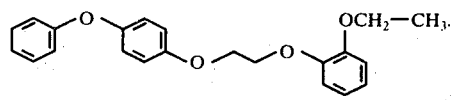

9. The compound according to claim 1 of the formula

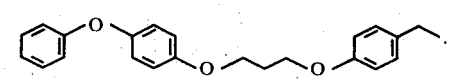

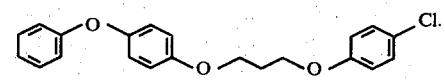

10. The compound according to claim 1 of the formula

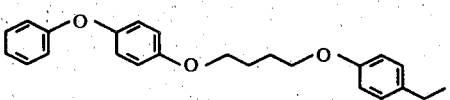

* * * * *